(12) United States Patent
Vadali et al.

(10) Patent No.: US 10,487,067 B2
(45) Date of Patent: Nov. 26, 2019

(54) PROCESS FOR THE PREPARATION OF VELPATASVIR

(71) Applicant: Mylan Laboratories Limited, Panvel (IN)

(72) Inventors: Lakshmana Rao Vadali, Panvel (IN); Sureshbabu Jayachandra, Panvel (IN); Rajasekhar Ponduri, Panvel (IN); Bhaskar Rao Padala, Panvel (IN); Eswara Reddy Yerva, Panvel (IN); Govardhana Phani Sharma Vemavarapu, Panvel (IN); Ravikanth Jaldu, Panvel (IN); Ramesh Dandala, Panvel (IN)

(73) Assignee: MYLAN LABORATORIES LIMITED (IN)

( * ) Notice: Subject to any disclaimer, the term of this patent is extended or adjusted under 35 U.S.C. 154(b) by 0 days.

(21) Appl. No.: 15/766,634

(22) PCT Filed: Oct. 5, 2016

(86) PCT No.: PCT/IB2016/055942
§ 371 (c)(1),
(2) Date: Apr. 6, 2018

(87) PCT Pub. No.: WO2017/060820
PCT Pub. Date: Apr. 13, 2017

(65) Prior Publication Data
US 2018/0282294 A1 Oct. 4, 2018

(30) Foreign Application Priority Data
Oct. 8, 2015 (IN) .......................... 3829/MUM/2015

(51) Int. Cl.
*C07D 311/78* (2006.01)
*C07D 311/80* (2006.01)
*C07C 45/63* (2006.01)
*C07D 491/052* (2006.01)
*C07C 45/45* (2006.01)

(52) U.S. Cl.
CPC .......... *C07D 311/78* (2013.01); *C07C 45/455* (2013.01); *C07C 45/63* (2013.01); *C07D 311/80* (2013.01); *C07D 491/052* (2013.01)

(58) Field of Classification Search
None
See application file for complete search history.

*Primary Examiner* — Heidi Reese

(57) ABSTRACT

The present disclosure provides a process for the preparation of velpatasvir intermediates. The intermediates may be further converted to velpatasvir or pharmaceutically acceptable salts thereof.

8 Claims, No Drawings

PROCESS FOR THE PREPARATION OF VELPATASVIR

CROSS-REFERENCE TO RELATED APPLICATIONS

This application claims the benefit of the earlier filing date of Indian Provisional Patent Application No. 3829/MUM/2015 filed on Oct. 8, 2015.

BACKGROUND OF THE INVENTION

Field of the Disclosure

The present disclosure relates to a process for the preparation of compounds of formulae 5 and 8. The compounds obtained by this process can be used for the preparation of the anti-hepatitis drug, velpatasvir.

Description of the Related Art

Velpatasvir is an inhibitor of NSSA often prescribed together with sofosbuvir in the treatment of hepatitis C infection. A combination drug containing velpatasvir and sofosbuvir is currently marketed as EPCLUSA® in the United States of America by Gilead Sciences. EPCLUSA® is indicated for the treatment of chronic hepatitis C virus (HCV) genotype 1, 2, 3, 4, 5, or 6 infection.

Velpatasvir is chemically named methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methyl pyrrolidin-1-yl]-3-methyl-1-oxobutan-2-yl}carbamate and is represented by the following chemical structure (I):

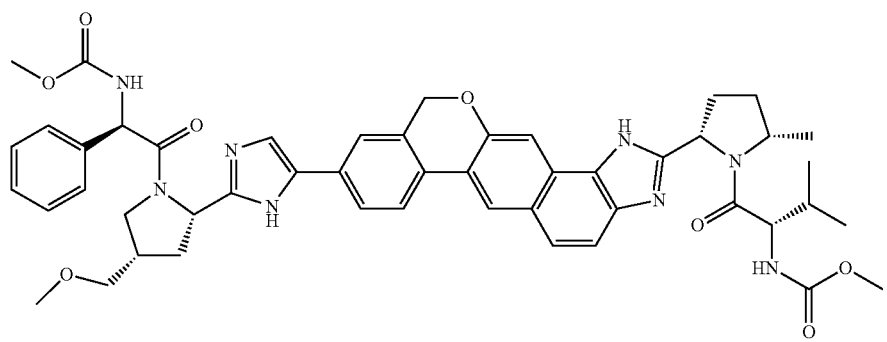

Velpatasvir is disclosed in U.S. Pat. No. 8,575,135 B2, which is hereby incorporated by reference.

The present disclosure provides a process for the preparation of intermediates that may be used in the preparation of velpatasvir.

SUMMARY OF THE DISCLOSURE

In a first aspect, the present disclosure provides a process for the preparation of compound of formula 5, which may include the following steps:

a) reacting the compound of formula 2 with a Grignard reagent to get a compound of formula 4; and

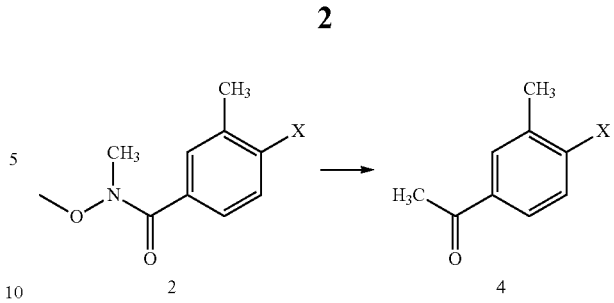

b) treating the compound of formula 4 with a halogenating agent to get the compound of formula 5.

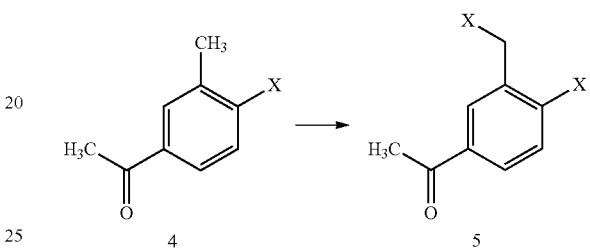

Within the context of this embodiment, each X is independently a halogen, for example, —F, —Cl, —Br, or —I.

Within the context of this embodiment, the halogenating agent may be, for example, N-bromosuccinimide, N-chlorosuccinimide, of N-iodosuccinimide, or liquid bromine. In some embodiments, the halogenating agent is N-bromosuccinimide.

Within the context of this embodiment, formula 4 may be converted to formula 5 in the presence of a catalyst. In some embodiments, this conversion is performed in the presence of benzoyl peroxide.

In a second aspect of the present disclosure, a process for the preparation of a compound of formula 8 is provided.

In one embodiment, formula 8 may be carried out by a process that includes the following steps:

a) reacting the compound of formula 2 with a Grignard reagent to get a compound of formula 4;

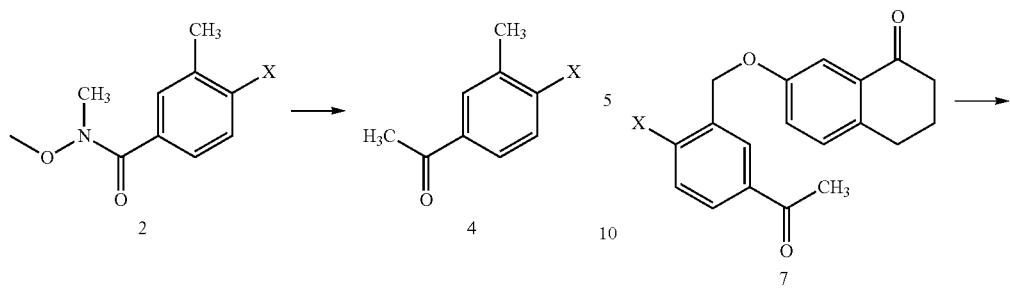

b) treating the compound of formula 4 with a halogenating agent to get the compound of formula 5;

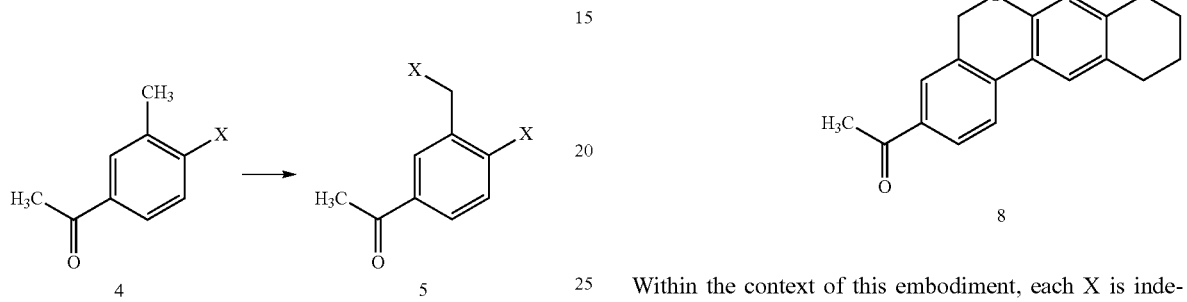

c) reacting the compound of formula 5 with a compound of formula 6 to get a compound of formula 7; and

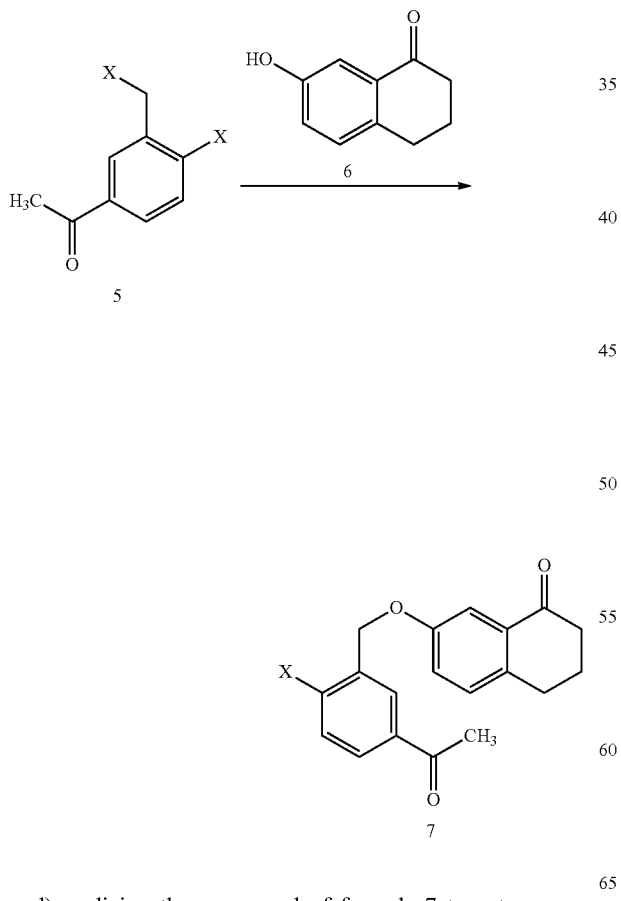

d) cyclizing the compound of formula 7 to get a compound of formula 8.

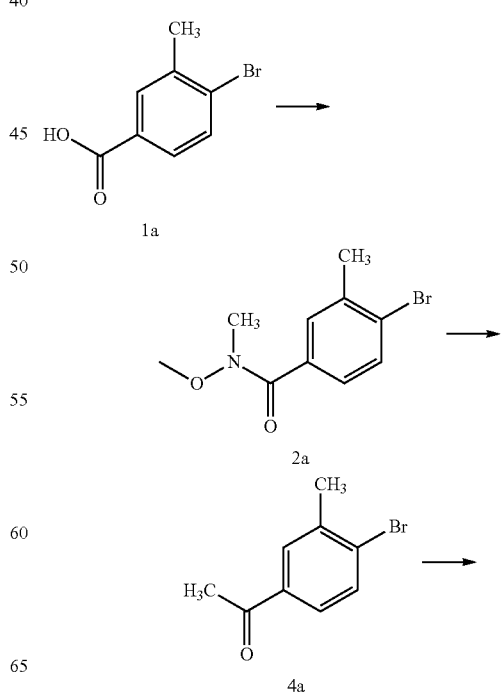

Within the context of this embodiment, each X is independently a halogen, for example, —F, —Cl, —Br, or —I.

Within the context of this embodiment, the halogenating agent may be, for example, N-bromosuccinimide, N-chlorosuccinimide, of N-iodosuccinimide, or liquid bromine. In some embodiments, the halogenating agent is N-bromosuccinimide.

Within the context of this embodiment, formula 4 may be converted to formula 5 in the presence of a catalyst. In some embodiments, this conversion is performed in the presence of benzoyl peroxide.

In a third aspect, the present disclosure provides a process for the preparation of compound of formula 8, which is as shown below.

5
-continued

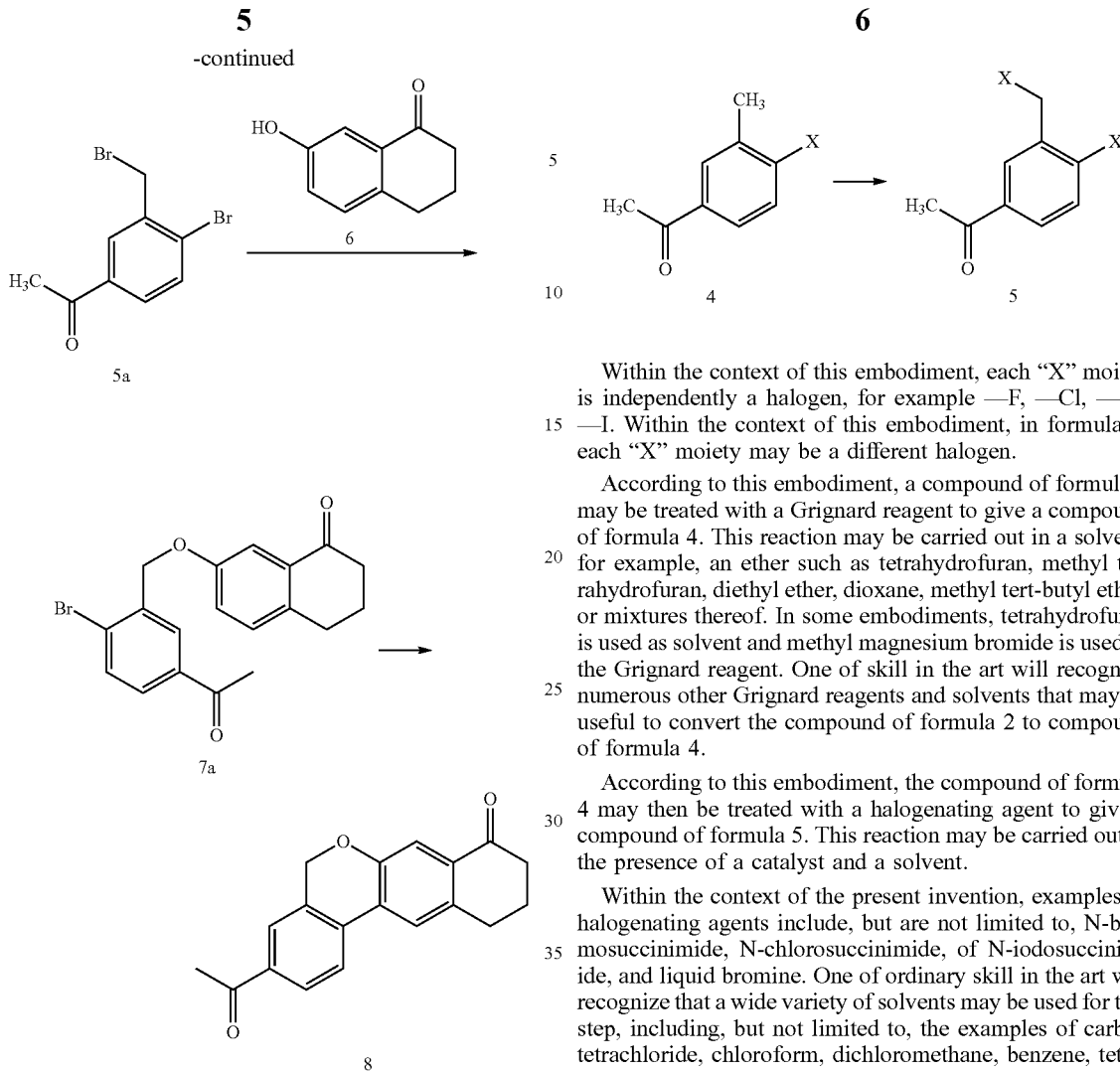

DETAILED DESCRIPTION OF THE INVENTION

In one aspect, the present invention provides a method for the preparation of a compound of formula 5.

In one embodiment, the compound of formula 5 may be prepared by a process that includes the following steps:

a) reacting the compound of formula 2 with a Grignard reagent to get a compound of formula 4; and

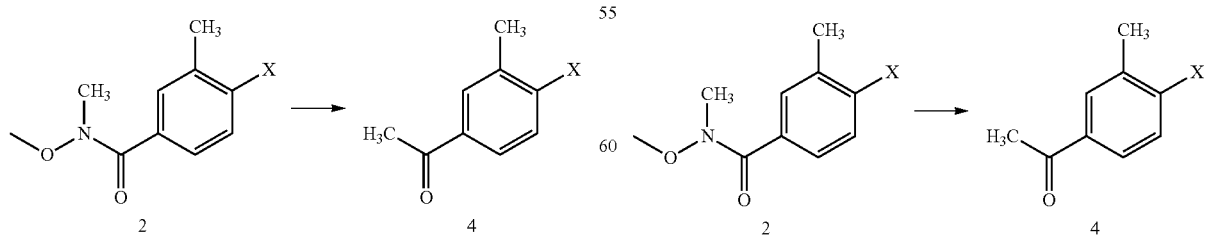

b) treating the compound of formula 4 with halogenating agent to get the compound of formula 5.

Within the context of this embodiment, each "X" moiety is independently a halogen, for example —F, —Cl, —Br, —I. Within the context of this embodiment, in formula 5, each "X" moiety may be a different halogen.

According to this embodiment, a compound of formula 2 may be treated with a Grignard reagent to give a compound of formula 4. This reaction may be carried out in a solvent, for example, an ether such as tetrahydrofuran, methyl tetrahydrofuran, diethyl ether, dioxane, methyl tert-butyl ether, or mixtures thereof. In some embodiments, tetrahydrofuran is used as solvent and methyl magnesium bromide is used as the Grignard reagent. One of skill in the art will recognize numerous other Grignard reagents and solvents that may be useful to convert the compound of formula 2 to compound of formula 4.

According to this embodiment, the compound of formula 4 may then be treated with a halogenating agent to give a compound of formula 5. This reaction may be carried out in the presence of a catalyst and a solvent.

Within the context of the present invention, examples of halogenating agents include, but are not limited to, N-bromosuccinimide, N-chlorosuccinimide, of N-iodosuccinimide, and liquid bromine. One of ordinary skill in the art will recognize that a wide variety of solvents may be used for this step, including, but not limited to, the examples of carbon tetrachloride, chloroform, dichloromethane, benzene, tetrahydrofuran, acetonitrile, or mixtures thereof. The catalyst may be, for example, benzoyl peroxide. In some embodiments, N-bromosuccinimide is used as halogenating agent and carbon tetrachloride is used as solvent. One of skill in the art will recognize numerous other halogenating agents and solvents that may be useful to convert the compound of formula 4 to compound of formula 5.

In another aspect, the present invention provides a process for the preparation of a compound of formula 8.

In one embodiment formula 8 may be prepared by a process that includes the following steps:

a) reacting the compound of formula 2 with a Grignard reagent to get a compound of formula 4;

b) treating the compound of formula 4 with a halogenating agent to get the compound of formula 5;

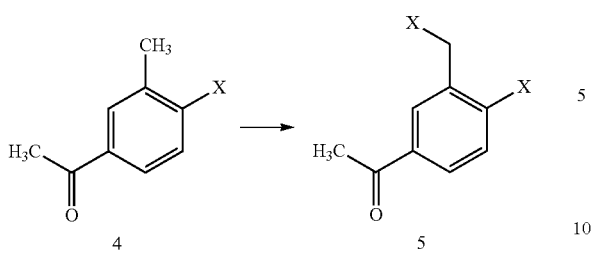

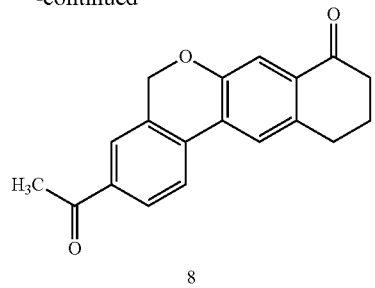

c) reacting the compound of formula 5 with a compound of formula 6 to get a compound of formula 7; and

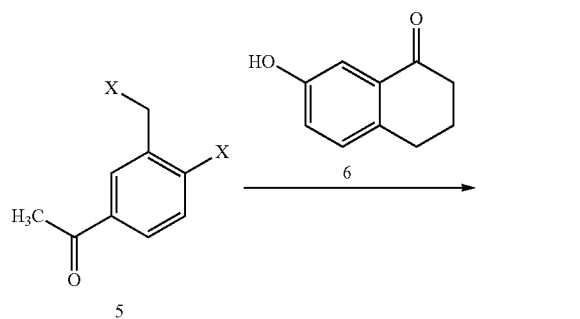

d) cyclizing the compound of formula 7 to get a compound of formula 8.

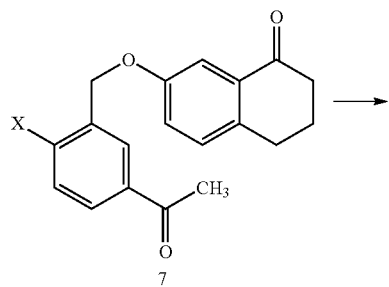

Within the context of this embodiment, each "X" moiety is independently a halogen, for example —F, —Cl, —Br, —I. Within the context of this embodiment, in formula 5, each "X" moiety may be a different halogen.

According to this embodiment, a compound of formula 2 may be treated with a Grignard reagent to give a compound of formula 4. This reaction may be carried out in a solvent, for example, an ether such as tetrahydrofuran, methyl tetrahydrofuran, diethyl ether, dioxane, methyl tert-butyl ether, or mixtures thereof. In some embodiments, tetrahydrofuran is used as solvent and methyl magnesium bromide is used as a Grignard reagent. One of skill in the art will recognize numerous other Grignard reagents and solvents that may be useful to convert the compound of formula 2 to compound of formula 4. Other Grignard reagents include, but are not limited to, alkyl magnesium halides (e.g., ethyl magnesium bromide, propyl magnesium chloride, and isopropyl magnesium bromide), alkenyl magnesium halides (e.g., propenyl magnesium bromide, vinyl magnesium chloride, and allyl magnesium chloride), and alkynyl magnesium halides (e.g., ethynyl magnesium bromide).

According to this embodiment of the present invention, compound of formula 4 is treated with halogenating agent to give a compound of formula 5. This reaction may be carried out in presence of a catalyst and solvent.

Within the context of the present invention, examples of suitable halogenating agents include, but are not limited to, N-bromosuccinimide, N-chlorosuccinimide, of N-iodosuccinimide, and liquid bromine. One of ordinary skill in the art will recognize that a wide variety of solvents may be used for this step, including, but not limited to, the examples of carbon tetrachloride, chloroform, dichloromethane, benzene, tetrahydrofuran, acetonitrile, or mixtures thereof. The catalyst may be, for example, benzoyl peroxide. In some embodiments of this present invention, N-bromosuccinimide is used as halogenating agent and carbon tetrachloride is used as solvent. One of skill in the art will recognize numerous other halogenating agents and solvents that may be useful to convert the compound of formula 4 to compound of formula 5.

According to this embodiment, the compound of formula 5 may be treated with a compound of formula 6 to get a compound of formula 7. This reaction may be carried out in presence of a base, a catalyst, and a solvent.

Within the context of this embodiment, examples of suitable bases include alkali metal carbonates and alkali metal hydroxides. Suitable alkali metal carbonates include, but are not limited to, lithium carbonate, sodium carbonate, potassium carbonate, cesium carbonate, and mixtures thereof. Suitable alkali metal hydroxides include, as examples, lithium hydroxide, sodium hydroxide, potassium hydroxide, cesium hydroxide, and mixtures thereof. In some embodiments, potassium carbonate is used as a base. One of skill in the art will recognize numerous other bases that may be useful for this reaction.

One of ordinary skill in the art will recognize that a wide variety of solvents may be used for this step, including, but not limited to, the examples of methanol, ethanol, water, methylene chloride, acetone, acetonitrile, ethyl acetate, tetrahydrofuran, N,N-dimethylformamide, N,N-dimethylacetamide, dimethyl sulfoxide, acetone, methyl isobutyl ketone, diisopropyl ether, toluene, and mixtures thereof. In some embodiments, a mixture of toluene and dimethyl sulfoxide is used as a solvent.

Within the context of this embodiment, examples of suitable catalysts include phase-transfer catalysts. Quaternary ammonium compounds, for example, may be used as a phase-transfer catalyst. Suitable quaternary ammonium compounds include, but are not limited to, tetrabutylammonium bromide, tetrabutylammonium iodide, tetrabutylammonium hydrogen sulfate, tetrabutylammonium fluoride trihydrate, tetrabutylammonium fluoride, and tetrabutylammonium chloride. In some embodiments, tetrabutylammonium bromide is used as phase transfer catalyst. One of skill in the art will recognize numerous phase-transfer catalysts that may be useful for this reaction.

According to this embodiment, compound of formula 7 may then be cyclized in the presence of a metal catalyst and a ligand to give a compound of formula 8. This reaction may be carried out in presence of an acid, a base, and a solvent.

Within the context of the present invention, examples of suitable metal catalysts include, but are not limited to, palladium(II) trifluoroacetate, palladium(II) acetylacetonate, allylpalladium(II) chloride dimer, palladium(II) acetate, palladium(II) pivalate, palladium(II) chloride, palladium(II) bromide, tris(dibenzylideneacetone)dipalladium, bis(dibenzylideneacetone)palladium, bis(acetonitrile)dichloropalladium(II).

Examples of suitable ligands include, but are not limited to, triphenylphosphine, 4-fluoro-triphenylphosphine, tricyclohexylphosphine, tri-(2-furyl)phosphine, tri-tert-butylphosphine, tri-tert-butylphosphine hydro tetrafluoroborate, methyl-di-tert-butylphosphine, methyl-di-tert-butylphosphine hydro tetrafluoroborate. In some embodiments, palladium(II) pivalate is used as a metal catalyst and 4-fluorotriphenylphosphine is used as a ligand. One of skill in the art will recognize numerous metal catalysts and ligands that may be useful to convert the compound of formula 7 to compound of formula 8.

Within the context of this embodiment, examples of suitable bases include, but are not limited to, lithium carbonate, sodium carbonate, cesium carbonate, magnesium carbonate, calcium carbonate, lithium hydroxide, sodium hydroxide potassium hydroxide, cesium hydroxide, magnesium hydroxide, calcium hydroxide, lithium bicarbonate, sodium bicarbonate, potassium bicarbonate, cesium bicarbonate, magnesium bicarbonate, calcium bicarbonate, lithium hydride, sodium hydride, potassium hydride, magnesium hydride, calcium hydride, lithium tert-butoxide, sodium tert-butoxide, potassium tert-butoxide, cesium tert-butoxide, magnesium tert-butoxide, calcium tert-butoxide, lithium acetate, sodium acetate, potassium acetate, cesium acetate, lithium isobutyrate, sodium isobutyrate, potassium isobutyrate, cesium isobutyrate. In some embodiments, potassium acetate is used as the base. One of skill in the art will recognize numerous bases that may be useful in cyclization reaction of compound of formula 7 to get compound of formula 8.

Within the context of this embodiment, suitable solvents include, but are not limited to, N,N-dimethylacetamide, N,N-dimethylformamide, acetonitrile, tetrahydrofuran, methyl tetrahydrofuran, and mixtures thereof. In some embodiments, N,N-dimethylacetamide is used as the solvent. One of skill in the art will recognize numerous solvents that may be useful in cyclization reaction of compound of formula 7 to get compound of formula 8.

Within the context of the present invention, the compound of formula 8 may be further converted into velpatasvir or pharmaceutically acceptable salts thereof. This may be performed by reactions well known in the art. For example, U.S. Pat. No. 8,575,135 discloses methods for the conversion of a compound of formula 8 to velpatasvir.

The intermediates formed during the processes disclosed herein can be characterized by $^1$H NMR analysis. Therefore, samples were analyzed by $^1$H NMR and data were collected on a Bruker 300 MHz Avance NMR spectrometer equipped with 5 mm BBI probe in $CDCl_3$. Data were collected and processed by Topsin-NMR software.

In some embodiments, the processes disclosed herein may utilize N-bromosuccinimide to prepare velpatasvir and intermediates thereof, thus providing an example of the numerous advantages of the presently disclosed invention. Specifically, the use of N-bromosuccinimide may reduce the number of steps undertaken during the synthetic process when compared to prior art processes that employ lithium bromide.

The velpatasvir as synthesized by the methods disclosed herein may be useful in the treatment of individuals infected with hepatitis C, as velpatasvir is an effective NS5A inhibitor. Velpatasvir may be used singly or in combination with other agents, such as sofosbuvir.

The velpatasvir along with optionally any other active ingredients, such as sofosbuvir, may be formulated as an oral dosage form, for example a tablet or a capsule. The tablet may include excipients, for example, copovidone, croscarmellose sodium, magnesium stearate, microcrystalline cellulose, and mixtures thereof. The tablet may, in some embodiments, be coated with a film that includes additional excipients, artificial flavorings, artificial colorings, and mixtures thereof. For example, the coating may contain iron oxide red, polyethylene glycol, polyvinyl alcohol, talc, titanium dioxide, or mixtures thereof.

In view of the above description and the examples below, one of ordinary skill in the art will be able to practice the invention as claimed without undue experimentation. The foregoing will be better understood with reference to the following examples that detail certain procedures for the preparation of molecules, compositions, and formulations according to the present invention. All references made to these examples are for the purposes of illustration. The following examples should not be considered exhaustive, but merely illustrative of only a few of the many aspects and embodiments contemplated by the present disclosure.

EXAMPLES

Example 1: Preparation of Formula 2a

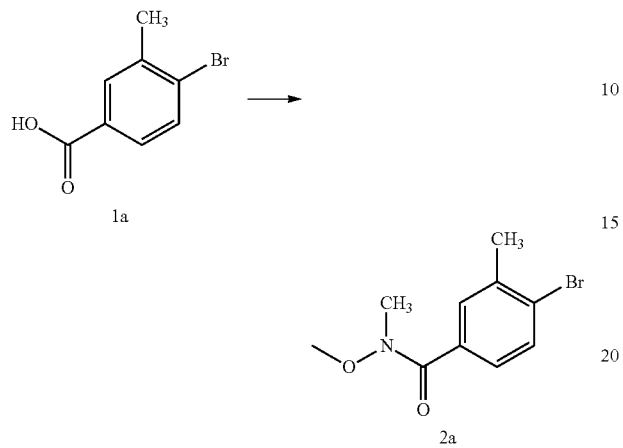

N,O-dimethylhydroxylamine hydrochloride (20 g), N-(3-dimethylaminopropyl)-N'-ethylcarbodiimide hydrochloride (3EDC.HCl) (20 g), and hydroxybenzotriazole (HOBt, 20 g) in dimethylformamide were added to a stirred solution of 4-bromo-3-methylbenzoic acid (formula 1a, 10 g) in diisopropylethylamine (20 g). After stirring at 25-35° C. for 16 hours, the reaction mixture was concentrated and purified by column chromatography (silica gel, 1:5 ethyl acetate:hexane) to give a compound of formula 2a as an off-white solid.

Example 2: Preparation of Formula 4a

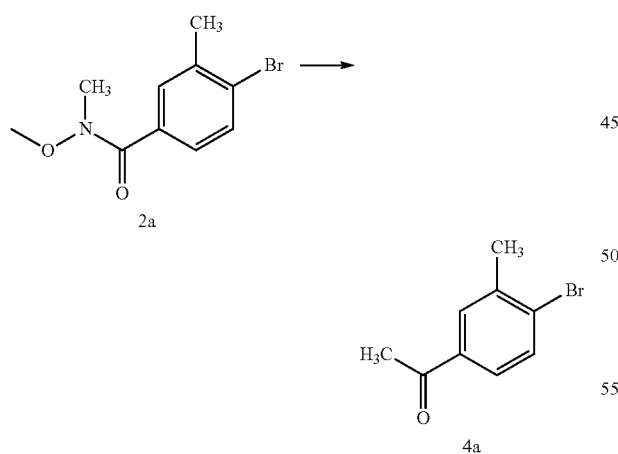

Methylmagnesium bromide solution in diethyl ether (3.0 M, 30.1 mL) was added to a stirred solution of a compound of formula 2a (20 g) in tetrahydrofuran at 0° C. The reaction mixture was allowed to warm to 25-35° C. and stirred at same temperature for 4 hours. The reaction mixture was quenched with an ammonium chloride solution and ethyl acetate was added. The organic layer was separated, washed with 1N HCl followed by water and concentrated. The obtained crude was purified by silica gel chromatography to afford 4-bromo-3-methylacetophenone (formula 4a) as an off-white solid.

$^1$H NMR (300 MHz, CDCl$_3$): 2.44 (s, 3H), 2.56 (s, 3H), 7.61 (s, 2H), 7.80 (s, 1H).

Example 3: Alternative Preparation of Formula 4a

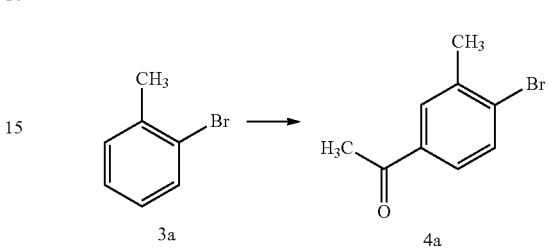

Aluminum chloride (9.5 g) was added in portion wise at 0° C. to a stirred solution of 2-bromotoluene (formula 3a, 10 g) in dichloromethane and stirred for 10 minutes. Then, acetyl chloride (5.5 g) was added drop wise at the same temperature. The resulting mixture was stirred for 2 hours while cooling with ice. Then the reaction mixture was added to 100 mL of 10% aq. hydrochloric acid solution, which was then allowed to separate into aqueous and organic layers. The organic layer thus obtained was washed with a 5% aqueous solution of sodium carbonate and dried over anhydrous sodium sulfate. The organic layer was concentrated and the obtained crude material was purified by fractional distillation to afford 4-bromo-3-methylacetophenone (formula 4a) as an off-white solid.

$^1$H NMR (300 MHz, CDCl$_3$): 2.44 (s, 3H), 2.56 (s, 3H), 7.61 (s, 2H), 7.80 (s, 1H).

Example 4: Preparation of Formula 5a

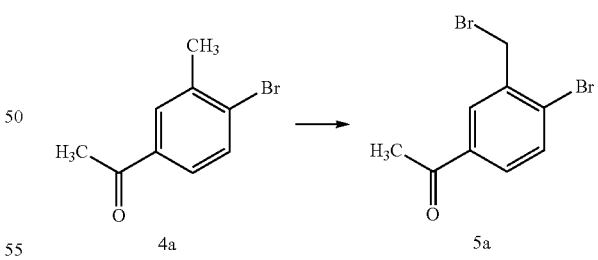

N-bromosuccanimide (4.17 g) was added to a solution of 4-bromo-3-methylacetophenone (formula 4a, 5 g) in carbon tetrachloride, followed by benzoyl peroxide (100 mg) and heated to reflux for 4 hours. After completion of the reaction, water (50 mL) was added and stirred for 10 minutes. The organic layer was separated, concentrated, and purified by column chromatography (silica gel, 5% ethyl acetate:hexane) to afford a compound of formula 5a as a white solid.

$^1$H NMR (300 MHz, CDCl3): 2.6 (s, 3H), 4.65 (s, 2H), 7.72 (m, 2H), 8.03 (d, 1H).

Example 5: Preparation of Formula 7a

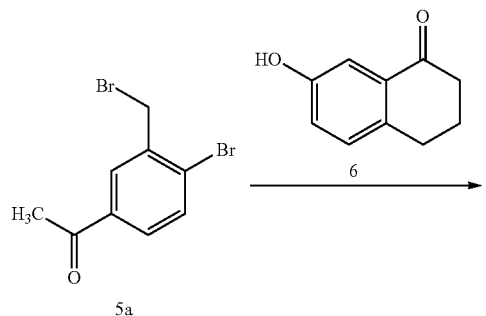

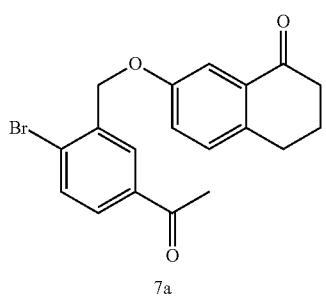

A compound of formula 5a (18 g), potassium carbonate (25.32 g), and tetrabutylammonium bromide (300 mg) were added to a solution of 7-hydroxytetralone (formula 6, 10 g) in toluene (90 mL) and dimethylsulfoxide (10 mL). The reaction mixture was stirred at 40° C. for 2 hours. After completion of the reaction, the reaction mixture was filtered and washed with carbon tetrachloride. Water (100 mL) was added to the filtrate and stirred for 10 minutes. The organic layer was separated and concentrated to afford a compound of formula 7 as an off-white solid.

$^1$H NMR (300 MHz, CDCl$_3$): 2.15 (m, 2H), 2.61 (s, 3H), 2.65 (t, 2H), 2.95 (t, 2H), 5.20 (s 2H), 7.2 (m, 2H), 7.62-7.80 (m, 3H), 8.12 (d, 2H).

Example 6: Preparation of Formula 8

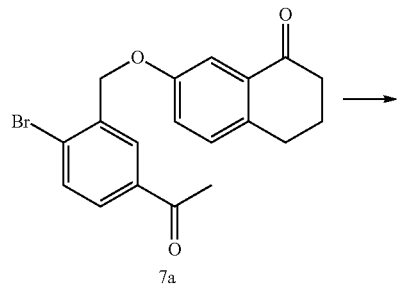

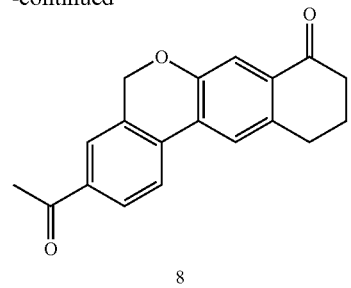

Pivalic acid (0.41 g), potassium acetate (3.91 g), Pd(II) pivalate (200 mg), and tris (4-Fluoro phenyl) phosphine (200 mg) were added to a stirred solution of a compound of formula 7a (10 g) in DMA. The reaction mixture was stirred at 90° C. for 1 hour. After completion of the reaction, water (100 mL) was added followed by dichloromethane (50 mL). The reaction mixture was stirred for 10 minutes, separated the organic layer, concentrated and purified by column chromatography (silica gel, 5% ethyl acetate:hexane) to afford a compound of formula 8 as a pale yellow color solid.

$^1$H NMR (300 MHz, CDCl$_3$): 2.15 (m, 2H), 2.61 (s, 3H), 2.65 (t, 2H), 3.00 (t, 2H), 5.15 (s, 2H), 7.65 (s, 2H), 7.80 (m, 2H), 8.0 (m, 1H).

The invention claimed is:

1. A process for the preparation of a compound of formula 5, comprising:
   a. reacting a compound of formula 2 with a Grignard reagent to get a compound of formula 4; and

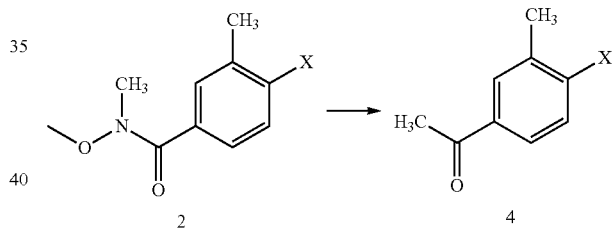

b. treating the compound of formula 4 with a halogenating agent to get a compound of formula 5,

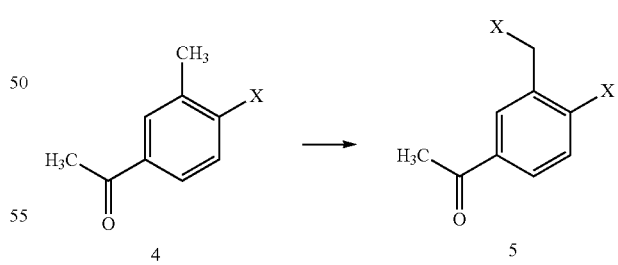

wherein each X is independently selected from the group consisting of —F, —Cl, —Br, and —I.

2. The process according to claim 1, wherein the halogenating agent is selected from the group consisting of N-bromosuccinimide, N-chlorosuccinimide, N-iodosuccinimide, and liquid bromine.

3. The process according to claim 1, wherein the treating of the compound of formula 4 with halogenating agent is further performed in the presence of benzoyl peroxide.

4. The process according to claim 1, further comprising:

a. reacting the compound of formula 5 with a compound of formula 6 to get a compound of formula 7; and b. cyclizing the compound of formula 7 to get a compound of formula 8,

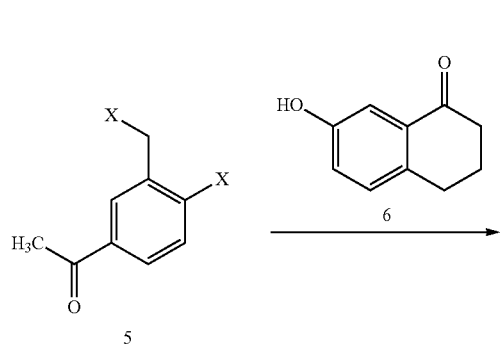

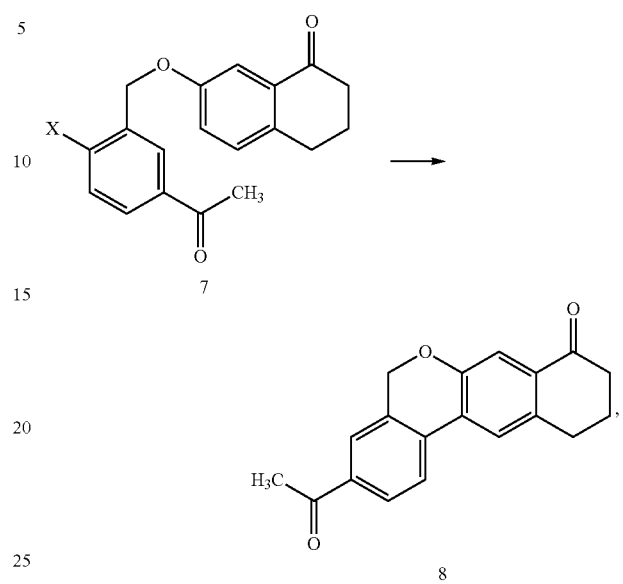

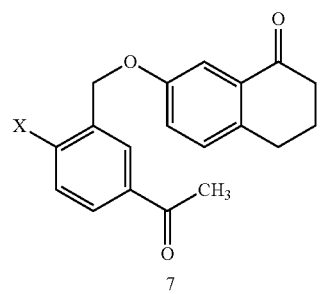

wherein each X is independently selected from the group consisting of —F, —Cl, —Br, and —I.

5. The process according to claim 1, further comprising converting the compound of formula 5 into velpatasvir.

6. The process according to claim 4, further comprising converting the compound of formula 8 into velpatasvir.

7. The process according to claim 5 further comprising converting velpatasvir into a pharmaceutically acceptable salt of velpatasvir.

8. The process according to claim 6 further comprising converting velpatasvir into a pharmaceutically acceptable salt of velpatasvir.

* * * * *